(12) United States Patent
Joos

(10) Patent No.: US 8,735,060 B2
(45) Date of Patent: May 27, 2014

(54) METHOD FOR ISOLATING HIGH-PURITY RNA BY MEANS OF PARAMAGNETIC MICROPARTICLES AND NANOPARTICLES

(75) Inventor: Hans Joos, Berlin (DE)

(73) Assignee: Stratec Molecular AG, Birkenfeld (DE)

( * ) Notice: Subject to any disclaimer, the term of this patent is extended or adjusted under 35 U.S.C. 154(b) by 24 days.

(21) Appl. No.: 13/386,941

(22) PCT Filed: Jul. 29, 2010

(86) PCT No.: PCT/DE2010/000916
§ 371 (c)(1),
(2), (4) Date: Jan. 25, 2012

(87) PCT Pub. No.: WO2011/012121
PCT Pub. Date: Feb. 3, 2011

(65) Prior Publication Data
US 2012/0123106 A1    May 17, 2012

(30) Foreign Application Priority Data
Jul. 29, 2009  (DE) .......................... 10 2009 035 643

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ......... 435/6.1; 435/6.11; 435/91.1; 536/23.1; 536/24.3; 536/24.33; 977/773

(58) Field of Classification Search
USPC ........... 435/6.1, 6.11, 91.1; 436/94; 536/23.1, 536/24.3; 977/773
See application file for complete search history.

(56) References Cited

U.S. PATENT DOCUMENTS

2005/0208510 A1 *  9/2005  Latham et al. .................... 435/6
2006/0177855 A1    8/2006  Utermohlen et al.
2009/0234112 A1 *  9/2009  Hillebrand ................... 536/55.3

FOREIGN PATENT DOCUMENTS

WO         2008/116225 A2     9/2008

OTHER PUBLICATIONS

Melzak et al., Driving Forces for DNA Adsorption to Silica in Perchlorate Solutions. Journal of Colloid and Interface Science, 181, 635-644, 1996.*
Zhao Xiaojun et al: "Collection of trace amounts of DNA/mRNA molecules using genomagnetic nanocapturers." in: Analytical Chemistry, vol. 75, No. 14, Jul. 15, 2003, pp. 3476-3483.
Tan Weihong et al: "Bionanotechnology based on silica nanoparticles" in: Medicinal Research Reviews, vol. 24, No. 5, Sep. 2004, pp. 621-638.
Otto P: "MagneSil(TM) paramagnetic particles: Magnetics for DNA purification" in: JALA—Journal of the Association for Laboratory Automation, vol. 7, No. 3, 2002, pp. 34-37.
Sonja Berensmeier: "Magnetic particles for the separation and purification of nucleic acids" in: Applied Microbiology and Biotechnology, vol. 73, No. 3, Oct. 25, 2006, pp. 495-504.
Tan S C et al: "DNA, RNA, and protein extraction: The past and the present" in: Journal of Biomedicine and Biotechnology, vol. 2009, 574398, Nov. 5, 2009, pp. 1-10.

* cited by examiner

*Primary Examiner* — Frank Lu
(74) *Attorney, Agent, or Firm* — Joyce von Natzmer; Agris & von Natzmer LLP

(57) ABSTRACT

The invention relates to a purification method for high-purity, DNA-free RNA using a mixture of nanocarrier beads and paramagnetic beads.

17 Claims, 13 Drawing Sheets

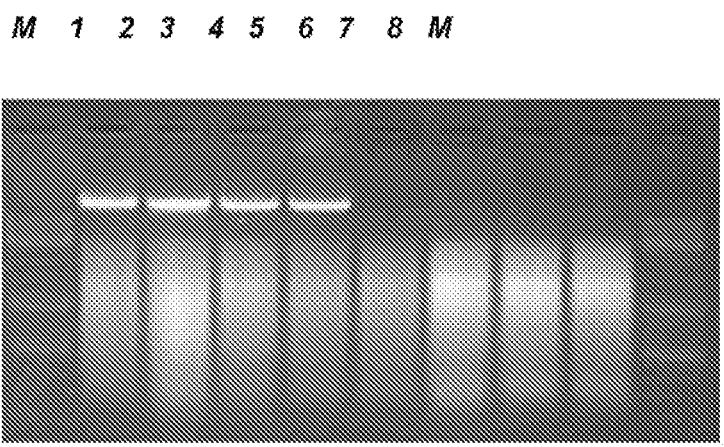
Figure 1: Gel, 1.2% DNA gel in 100 µl of elution buffer R, 20 µl

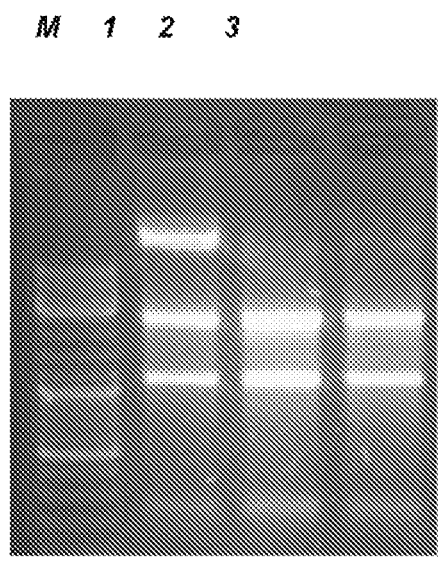
Figure 2: Gel, 1.2% RNA gel in 100 µl of elution buffer R, 20 µl + 2 µl of formamide for 10 min at 70°C

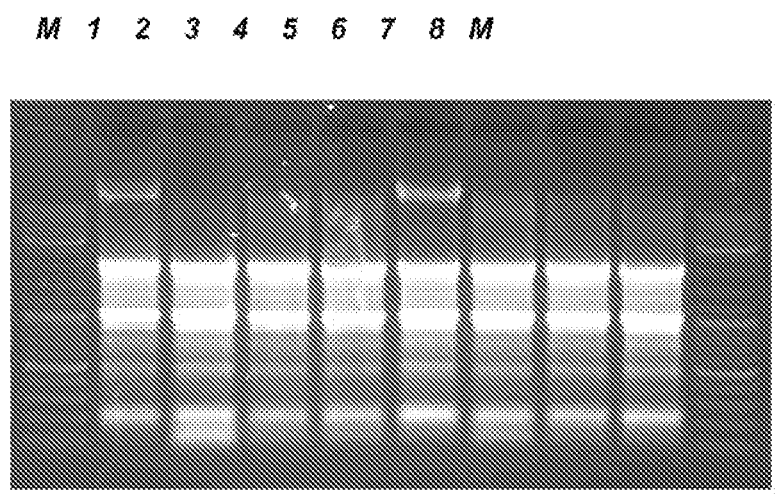
Figure 3: Gel, 1.2% RNA gel in 100 µl of elution buffer R, 20 µl + 2 µl of formamide for 10 min at 70°C

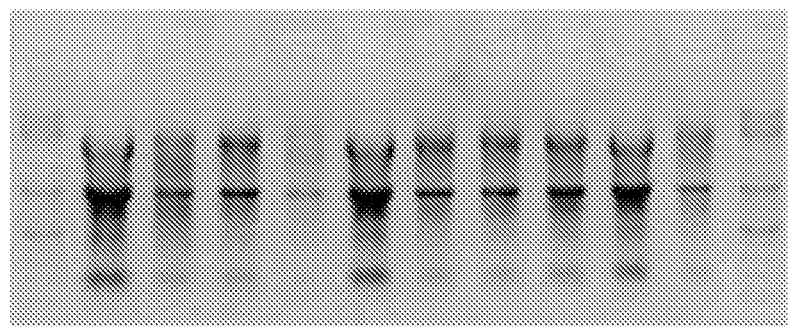
Figure 4: Liver, RNA gel 1%

| Sample ID | User ID | Date | Time | ng/µl | A:260 | A:280 | 260/280 | 260/230 | Constant | Cursor Pos. | Cursor abs. | 340 raw |
|---|---|---|---|---|---|---|---|---|---|---|---|---|
| Leber 1 | Default | 4/22/2010 | 12:12 PM | 902.09 | 22.552 | 10.781 | 2.09 | 1.82 | 40.00 | 230 | 12.369 | 1.031 |
| Leber 1 | Default | 4/22/2010 | 12:12 PM | 907.12 | 22.678 | 10.771 | 2.11 | 1.62 | 40.00 | 320 | 0.140 | 1.132 |
| Leber 2 | Default | 4/22/2010 | 12:12 PM | 223.40 | 5.585 | 2.708 | 2.06 | 0.87 | 40.00 | 330 | 0.043 | 0.281 |
| Leber 2 | Default | 4/22/2010 | 12:13 PM | 230.29 | 5.757 | 2.788 | 2.06 | 0.89 | 40.00 | 230 | 6.551 | 0.371 |
| Leber 3 | Default | 4/22/2010 | 12:14 PM | 293.74 | 5.844 | 2.804 | 2.08 | 1.03 | 40.00 | 320 | 5.676 | 0.171 |
| Leber 3 | Default | 4/22/2010 | 12:14 PM | 242.19 | 6.053 | 2.930 | 2.07 | 1.01 | 40.00 | 320 | 0.036 | 0.187 |
| Leber 4 | Default | 4/22/2010 | 12:29 PM | 63.26 | 1.582 | 0.751 | 2.10 | 0.35 | 40.00 | 320 | 0.012 | 0.052 |
| Leber 4 | Default | 4/22/2010 | 12:29 PM | 129.97 | 3.249 | 1.541 | 2.11 | 0.55 | 40.00 | 320 | 5.901 | 0.112 |
| Leber 5 | Default | 4/22/2010 | 12:30 PM | 708.39 | 17.710 | 8.365 | 2.12 | 1.59 | 40.00 | 230 | 11.123 | 0.347 |
| Leber 5 | Default | 4/22/2010 | 12:30 PM | 697.32 | 17.433 | 8.131 | 2.14 | 1.52 | 40.00 | 330 | 0.072 | 1.099 |
| Leber 6 | Default | 4/22/2010 | 12:31 PM | 178.32 | 4.458 | 2.156 | 2.07 | 1.23 | 40.00 | 330 | 0.026 | 0.114 |
| Leber 6 | Default | 4/22/2010 | 12:31 PM | 191.04 | 4.776 | 2.284 | 2.09 | 1.23 | 40.00 | 230 | 3.871 | 0.136 |
| Leber 7 | Default | 4/22/2010 | 12:32 PM | 208.20 | 5.205 | 2.493 | 2.09 | 1.07 | 40.00 | 230 | 4.650 | 0.158 |
| Leber 7 | Default | 4/22/2010 | 12:32 PM | 212.95 | 5.324 | 2.574 | 2.07 | 1.07 | 40.00 | 330 | 0.091 | 0.159 |
| Leber 8 | Default | 4/22/2010 | 12:32 PM | 260.89 | 6.747 | 3.255 | 2.08 | 1.11 | 40.00 | 320 | 0.025 | 0.164 |
| Leber 8 | Default | 4/22/2010 | 12:33 PM | 274.98 | 6.874 | 3.312 | 2.08 | 1.10 | 40.00 | 230 | 8.202 | 0.200 |
| Leber 9 | Default | 4/22/2010 | 12:33 PM | 531.49 | 13.287 | 6.197 | 2.14 | 1.54 | 40.00 | 230 | 8.642 | 0.745 |
| Leber 9 | Default | 4/22/2010 | 12:34 PM | 530.21 | 13.255 | 6.187 | 2.14 | 1.52 | 40.00 | 230 | 9.089 | 0.619 |
| Leber 10 | Default | 4/22/2010 | 12:34 PM | 109.90 | 2.747 | 1.331 | 2.06 | 1.17 | 40.00 | 320 | 0.017 | 0.043 |
| Leber 10 | Default | 4/22/2010 | 12:34 PM | 124.40 | 3.110 | 1.485 | 2.09 | 1.16 | 40.00 | 230 | 2.679 | 0.084 |

Figure 5. Photometric measurement (liver)

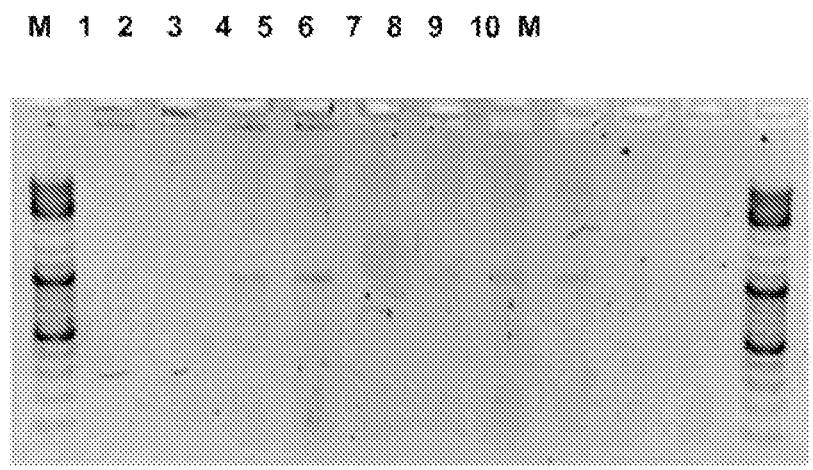
Figure 6: Stomach, RNA gel 1%

Figure 7: Photometric measurement (stomach)

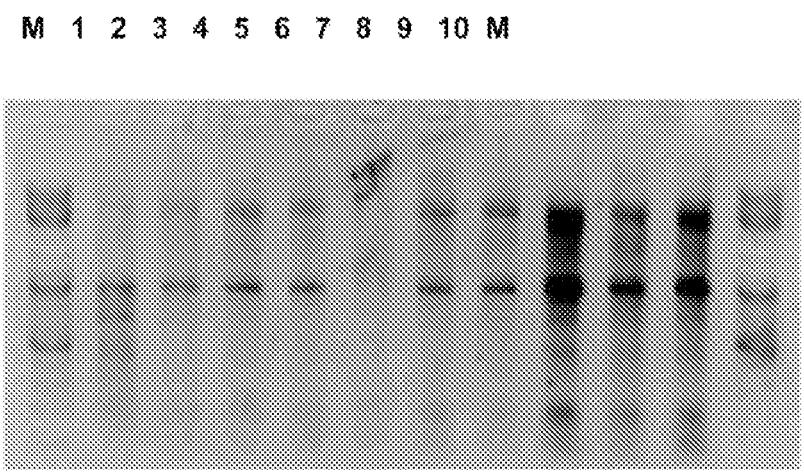
Figure 8: Kidney, RNA gel 1%

Figure 9: Photometric measurement (kidney)

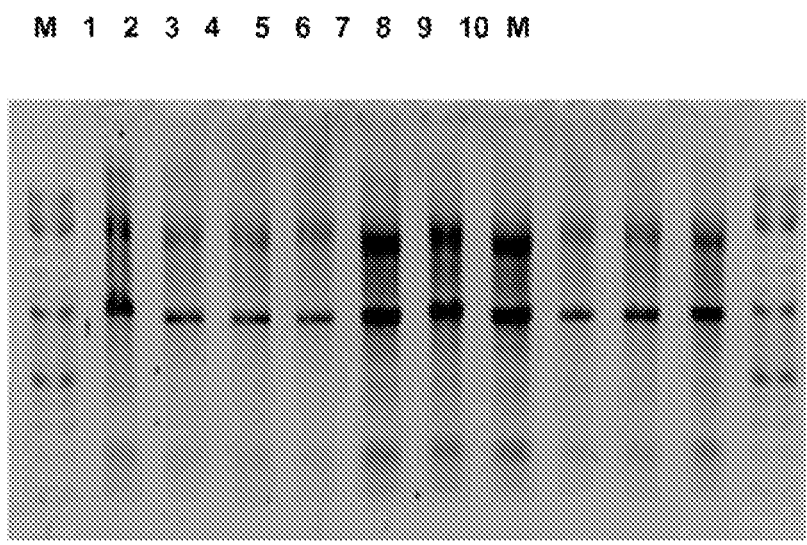
Figure 10: Brain, RNA gel 1%

Figure 11: Photometric measurement (brain)

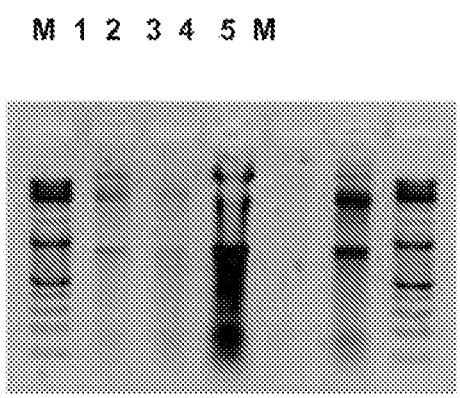
Figure 12: Intestine, RNA gel 1%

| Sample ID | User ID | Date | Time | ng/ul | A260 | A280 | 260/280 | 260/230 | Constant | Cursor Pos. | Cursor abs. | 340 raw |
|---|---|---|---|---|---|---|---|---|---|---|---|---|
| DNA Darm 1 | Default | 6/17/2010 | 2:24 PM | 27.86 | 0.580 | 0.251 | 2.23 | 0.25 | 50.00 | 230 | 2.219 | 0.085 |
| DNA Darm 1 | Default | 6/17/2010 | 2:24 PM | 26.00 | 0.520 | 0.222 | 2.34 | 0.24 | 50.00 | 320 | -0.002 | 0.114 |
| RNA Darm 1 | Default | 6/17/2010 | 2:25 PM | 21.29 | 0.532 | 0.238 | 2.23 | 0.23 | 40.00 | 320 | -0.001 | 0.098 |
| RNA Darm 1 | Default | 6/17/2010 | 2:25 PM | 22.60 | 0.560 | 0.241 | 2.29 | 0.23 | 40.00 | 230 | 2.371 | 0.171 |
| DNA Darm 2 | Default | 6/17/2010 | 2:26 PM | 20.12 | 0.402 | 0.155 | 2.60 | 0.31 | 50.00 | 230 | 1.892 | -0.012 |
| DNA Darm 2 | Default | 6/17/2010 | 2:26 PM | 21.41 | 0.428 | 0.177 | 2.41 | 0.21 | 50.00 | 320 | -0.014 | 0.002 |
| RNA Darm 2 | Default | 6/17/2010 | 2:26 PM | 18.22 | 0.456 | 0.188 | 2.43 | 0.22 | 40.00 | 320 | -0.008 | 0.001 |
| RNA Darm 2 | Default | 6/17/2010 | 2:27 PM | 19.77 | 0.489 | 0.196 | 2.39 | 0.22 | 40.00 | 230 | 2.178 | 0.026 |
| DNA Darm 3 | Default | 6/17/2010 | 2:27 PM | 384.60 | 7.692 | 3.742 | 3.05 | 1.30 | 50.00 | 230 | 0.380 | 0.153 |
| DNA Darm 3 | Default | 6/17/2010 | 2:28 PM | 380.63 | 7.613 | 3.722 | 2.05 | 1.19 | 50.00 | 320 | 0.612 | 0.139 |
| RNA Darm 3 | Default | 6/17/2010 | 2:28 PM | 299.00 | 7.475 | 3.641 | 2.05 | 1.16 | 40.00 | 320 | -0.001 | 0.129 |
| RNA Darm 3 | Default | 6/17/2010 | 2:29 PM | 298.22 | 7.455 | 3.615 | 2.06 | 1.15 | 40.00 | 230 | 6.568 | 0.115 |
| DNA Darm 4 | Default | 6/17/2010 | 2:29 PM | 5.51 | 0.110 | 0.025 | 4.33 | 0.04 | 50.00 | 230 | 3.847 | 0.005 |
| DNA Darm 4 | Default | 6/17/2010 | 2:30 PM | 63.15 | 1.263 | 0.601 | 2.10 | 0.33 | 50.00 | 320 | -0.009 | 0.026 |
| RNA Darm 4 | Default | 6/17/2010 | 2:30 PM | 70.87 | 1.764 | 0.844 | 2.09 | 0.41 | 40.00 | 320 | -0.011 | 0.058 |
| RNA Darm 4 | Default | 6/17/2010 | 2:30 PM | 68.92 | 1.723 | 0.817 | 2.11 | 0.40 | 40.00 | 230 | 4.329 | 0.058 |
| DNA Darm 5 | Default | 6/17/2010 | 2:31 PM | 127.17 | 2.543 | 1.198 | 2.12 | 0.30 | 50.00 | 230 | 2.833 | 0.035 |
| DNA Darm 5 | Default | 6/17/2010 | 2:31 PM | 136.75 | 2.735 | 1.281 | 2.13 | 0.83 | 50.00 | 320 | -0.003 | 0.036 |
| RNA Darm 6 | Default | 6/17/2010 | 2:32 PM | 109.96 | 2.749 | 1.262 | 2.18 | 0.82 | 40.00 | 320 | -0.004 | 0.005 |
| RNA Darm 6 | Default | 6/17/2010 | 2:32 PM | 110.33 | 2.758 | 1.252 | 2.20 | 0.80 | 40.00 | 230 | 3.468 | 0.029 |

Figure 13: Photometric measurement (intestine)

METHOD FOR ISOLATING HIGH-PURITY RNA BY MEANS OF PARAMAGNETIC MICROPARTICLES AND NANOPARTICLES

CROSS-REFERENCE TO RELATED APPLICATIONS

This is the U.S. national stage of International application PCT/DE2010/000916, filed Jul. 29, 2010 designating the United States, claiming priority to German application DE 10 2009 035 643.6, filed Jul. 29, 2009.

DESCRIPTION

To date, isolation of total RNA from biological starting materials without simultaneous purification of at least small amounts of DNA has been achieved in only a few practicable methods. In most cases it must be assumed that the isolated cellular total RNA is contaminated with genomic DNA.

A large number of RNA isolation protocols therefore recommend a step including a DNA-degrading enzyme, e.g. DNase I, which in turn renders the procedure particularly lengthy and costly.

The techniques of isolating total RNA have originally developed on the basis of protocols involving the use of phenol and chloroform, wherein a two-phase system of organic phase and aqueous phase is used under suitable conditions. While proteins and DNA bound thereto accumulate in the organic phase or at the boundary between organic phase and aqueous phase, the RNA remains in the aqueous phase, from which it can then be precipitated in the acidic range using ethanol or isopropanol (e.g. Chomczynski, P., Biotechniques 1993, 15(3): 532-536). The main drawback of these methods lies in the use of the highly toxic and carcinogenic substances chloroform and phenol.

Another option for the separate isolation of pure RNA basically involves performing an ultracentrifugation using a cesium chloride gradient to pelletize the RNA, while the DNA remains in the guanidinium phase (Coombs L. M., Pigott D., Proctor, A., Eydmann, M., Denner, J., and Knowles, M. A., Anal. Biochem. (1990), 188, 338-343). However, such a process requires a substantial input of time (at least 48 hours) and cost (ultracentrifugation techniques, special rotors).

A simplified method for the simultaneous and separate isolation of DNA and RNA has been disclosed in the laid-open document WO 9728171 A1. Therein, the biological sample is lysed with a chaotropic buffer. Lysis is followed by addition of nanoparticles (smaller than 40 nm) consisting of a monodisperse silicon material. The genomic DNA binds to these particles. The batch is subsequently centrifuged to pelletize the silicon particles. The remaining supernatant is then subjected to a conventional phenol/chloroform extraction, and the RNA is eventually precipitated in this way and dissolved after washing steps using water. While this method has the advantage of saving time compared to the methods described above, it involves working with highly toxic and carcinogenic groups of substances such as chloroform and phenol.

One modification of this method is replacing the phenol/chloroform purification by a purification using a spin filter with silica membranes. Another step forward in this method is that the nanoparticles with bound DNA can also be removed by filtration. However, it is here where this method encounters its limits, because viscous solutions in association with nanoparticles frequently give rise to filter clogging and termination of the process. This can only be counteracted by strictly limiting the employed amounts of biomaterials for extraction.

DE 102006031764 A1 describes a method for the parallel isolation of double-stranded and single-stranded nucleic acids. In this method, the double-stranded nucleic acid is adjusted with an aqueous salt solution at a concentration of greater than 1 M in such a way that the double-stranded nucleic acid is adsorbed on a solid support, while the single-stranded nucleic acid is not adsorbed and remains in the solution. Thereafter, the single-stranded nucleic acid can be purified from the flow of a spin filter by adjusting the binding conditions. However, the restriction with respect to the employed amounts of biomaterials applies in this case as well. Another disadvantage is that small amounts of DNA are regularly found in samples in this method as well.

Limitations as to the amount of nucleic acid can be avoided by using paramagnetic beads with a silica or silica-like hydrophilic surface. To date, a wide variety of applications involving the use of such particles to isolate nucleic acids have been described for both DNA and RNA. One such method for the purification of DNA has been disclosed in WO 2005021748 A1.

In many of these methods the desired nucleic acid is bound to the surface of the beads using suitable salt-alcohol mixtures, washed using other suitable salt-alcohol mixtures, and subsequently eluted in a low-salt buffer. The conditions are adjusted for binding DNA (double-stranded nucleic acid) or RNA (single-stranded nucleic acid), respectively.

The biological sample is dissolved in a buffer containing antichaotropic salts, proteolytic enzymes and detergents. Following lysis, a suitable binding environment is adjusted by adding a buffer containing alcohol. This is followed by addition of paramagnetic beads to which the RNA binds. Wash steps using alcoholic wash buffers are performed to wash off contaminations such as proteins and salts. Thereafter, the beads are dried, and the RNA is subsequently eluted in water. During this process the beads are transported by a magnetic separator from one buffer to the next. One limitation of the method using paramagnetic beads is the lacking option of quantitative removal of DNA by binding when preparing an RNA. The efficiency of DNA removal is as high as 90%, but this does not at all meet the high demands on DNA-free RNA.

The removal of DNA can be achieved via formation of a complex with nanomaterials (e.g. WO 9728171 A1). However, materials of such a size cannot be provided with sufficient iron oxide cores so as to allow removal from solutions by acceptable magnetic separators within acceptable periods of time. Thus, separation times of more than 30 minutes or magnetic fields in the 1 Tesla range are not acceptable, firstly because of the duration of the procedure, and secondly because of the costs and risks associated with the separator.

The isolation of DNA-free RNA is important in a variety of biological, medical and analytical fields. In particular, chip technologies being used in many diagnostic fields require relatively large amounts of RNA in DNA-free state. For this reason, there is a great demand for a safe, rapid and cost-effective method.

In light of the prior art, the problem forming the basis of this invention is to provide a method for the purification of high-purity, DNA-free RNA, which method overcomes the disadvantages of the prior art.

BRIEF DESCRIPTION OF THE DRAWINGS

FIG. 1 shows complete removal of the DNA when using a combination of paramagnetic beads and nanocarrier beads on selected lanes of the gel shown;

FIG. 2 shows complete removal of DNA on the gel shown when using beads A;

FIG. 3 shows paramagnetic beads alone barely remove any DNA;

FIG. 4 shows DNA removal in rat liver,

FIG. 5 shows the corresponding photometric measurements;

FIG. 6 shows DNA removal in the stomach,

FIG. 7 shows the corresponding photometric measurements;

FIG. 8 shows DNA removal in the kidney,

FIG. 9 shows the corresponding photometric measurements;

FIG. 10 shows DNA removal in the brain,

FIG. 11 shows the corresponding photometric measurements;

FIG. 12 shows DNA removal in the intestine,

FIG. 13 shows the corresponding photometric measurements.

DETAILED DESCRIPTION OF THE INVENTION

The problem forming the basis of this invention is solved by the method of the main claim. Preferred variants are shown in the subclaims.

In a first embodiment the invention relates to a method for the purification of RNA from a biological sample, said method comprising
- contacting the sample with a lysis buffer, nanocarrier beads and magnetizable beads, preferably paramagnetic beads,
- separating the DNA by means of a magnetic field,
- adding a binding buffer,
- isolating the RNA.

It was surprising that the use of a mixture of nanocarrier beads and paramagnetic beads allows binding of the total DNA from a sample. Removal of the total amount of DNA from a biological sample in a simple, rapid and cost-effective manner to obtain DNA-free RNA has not been possible as yet.

In the meaning of the invention the term "nanocarrier beads" describes granular silicon oxide, preferably a silicon dioxide having a grain size of 50 nm. Other suitable nanocarrier beads are granular silicon oxides having a grain size of from 10 to 200 nm or other granular substances having a grain size of from 10 to 200 nm and hydrophilic surface, e.g. granular substances having a grain size of from 10 to 200 nm and surfaces containing —COOH groups. It is preferred that nanocarrier beads are substantially non-magnetic.

Referred to as "paramagnetic beads" in accordance with the invention are particles having a paramagnetic or superparamagnetic core and a hydrophilic surface. The hydrophilic surface preferably comprise of silicon oxide, primary amines ($NH_2$), carboxylic acids (COOH) or hydroxyl groups (OH). In a preferred fashion the paramagnetic beads have a grain size of >200 nm, more preferably 1-2 µm. It is also preferred that the core of the paramagnetic beads comprise of iron oxide. In addition, the surface of the paramagnetic beads advantageously comprises silica.

It is also possible to use other magnetizable beads. In the context of the invention the term "magnetizable" means that the support can have a magnetic moment when exposed to a magnetic field and thus can be moved under the effect of this field.

The effectiveness of magnetizable particles used in prior art separation applications essentially depends on two factors. On the one hand, the particles should have a magnetic moment as high as possible so as to allow removal using small magnetic field gradients. On the other hand, however, the number of binding sites available to the nucleic acid must be as high as possible so as to have preferably complete separation thereof.

Many commercially available particles are based on multicore particles. Owing to the dispersion of a large number of primary particles within a polymer matrix, they show strong interaction with an external magnetic field, thereby allowing easy removal. At the same time, however, they have a relatively small volume-to-surface ratio, so that the maximum number of binding sites is limited. In addition, such particles tend to undergo rapid sedimentation, thereby further hampering effective binding. In contrast, smaller, separately enveloped particles have a very large surface area in relation to their volume and sediment much more slowly. The binding capacity for the target structure is therefore far superior compared to the multicore particles. However, the disadvantage is that, due to the lower magnetic moment, particularly high field gradients must be used to separate the particles from the mixture. On the one hand, this necessitates expensive equipment, and, on the other hand, particularly high magnetic field gradients invariably imply safety risks and impaired quality. As a consequence, the prior art methods for magnetic separation always demand a compromise between easy removability and completeness of removal of bound material.

The invention solves this problem by using two different particles. On the one hand, it is preferred to use non-magnetic nanocarrier beads so as to have complete and firm DNA crosslinking. On the other hand, magnetizable particles, preferably paramagnetic beads, are used, which in fact do not have particularly good crosslinking properties, but allow easy and safe removal in a relatively weak or moderate magnetic field. In a preferred fashion the magnetizable particles can be paramagnetic beads, superparamagnetic beads and/or multicore particles.

The invention is based on adjusting conditions in the lysis buffer that are suitable for the formation of a complex of nanocarrier beads, preferably particulate silicate nanocarriers, paramagnetic beads, preferably having silica surfaces, and DNA. The RNA contained in the mixture does not form part of the complex. The complex is removed from the mixture using purification by magnetic separation. This is followed by a standard RNA isolation method, preferably using magnetizable beads.

It is particularly advantageous that the method of the invention performs without the use of the toxic and carcinogenic substances phenol and chloroform. As a result, the safety of workers involved is improved many times over, and the quality of the isolated RNA is improved as well.

The complex can be removed particularly easily via magnetic aggregation. This procedure is much more gentle than traditional techniques such as centrifugation. Centrifugation invariably gives rise to shear forces that can dissolve the cells or degrade the nucleic acid. The method of the invention therefore allows more careful isolation of RNA, and the risk of RNA degradation during the process is reduced many times over.

There are two differences between DNA and RNA that have been utilized in prior art purification and separation methods. Common methods either solely utilize the difference between single-stranded and double-stranded nucleic acids, which is achieved via selective surface binding, or utilize the difference in molecular weights. DNA is much longer than RNA, and in the case of genomic human DNA, all fragments are several 100,000 bases in length. This difference is utilized in separation methods using gels and centrifugations.

Surprisingly, the method according to the invention can utilize both differences, which furnishes significantly improved results. The method of the invention is easy to use and requires no expensive equipment or reagents.

In a preferred manner, there is formation of a complex of nanocarrier beads, DNA and paramagnetic beads. The high binding affinity of DNA to nanocarrier beads has already been known from DE 195 06 887. However, it was a complete surprise that a crosslinked complex is formed with this carrier and long-chain DNA. This complex forms in such a way that one DNA molecule binds a plurality of carrier particles and one carrier particle in turn binds a plurality of DNA molecules. In essence, this surprising effect enables complete removal of the total DNA from the sample in a single step.

By virtue of a fortunate choice, there was the surprising advantage that resulted from the addition of paramagnetic beads. The paramagnetic beads also bind to the DNA, so that the complex is bound as a whole. To this end, the buffer should be adjusted so as to have good binding conditions for the DNA. Those skilled in the art will be able to produce an appropriate buffer without requiring their own inventive activity. A buffer having a moderately high salt concentration is preferred. As a result, the paramagnetic beads will bind to the DNA, but not to the RNA. It is possible in this way to remove the entire complex (nanocarrier beads, DNA, paramagnetic beads) with a relatively weak magnetic field, so that no DNA or non-magnetic nanocarrier beads remain. This is a great advantage over conventional methods wherein binding of DNA to paramagnetic beads proceeds via individual DNA strands. The invention allows more effective, easy, and complete removal of the total DNA.

Surprisingly, a mixture of nanocarrier beads and magnetizable beads, preferably paramagnetic beads, results in efficient binding of the DNA, while the use of the individual components cannot achieve sufficient separation.

DNA is a very long-chained molecule and therefore ideally suited for such a complex type of crosslinking. Even if the buffer conditions were adjusted in such a way that the RNA could bind, it would not be crosslinked due to the short single strands and therefore remain in solution. The method according to the invention therefore ensures that the RNA remains in solution, so that losses are avoided, which is especially important in those cases where only a small amount of sample material is available. On the one hand, the binding conditions are not ideal for RNA, and, on the other hand, the RNA is not capable of complex formation due to its shortness. Two different properties of the two nucleic acids are cooperatively involved in the selection, and it is only in this way that DNA-free RNA can remain in solution to be purified later using a conventional magnetic separation protocol, such as described in Appl. Microbiol. Biotechnol. (2006) 73: 495-504; Sonja Berensmeier: Magnetic particles for the separation and purification of nucleic acids. Thus, the invention provides a method by means of which DNA-free RNA can be obtained without centrifugation steps.

It is also preferred that the purified RNA is essentially free of DNA. In the meaning of the invention, "RNA essentially free of DNA" refers to a purity level of more than 90%, preferably 95 to 100%. High purity of RNA without DNA contaminations is required in various fields of applications, so that the invention has great economic importance.

In another preferred embodiment the invention relates to said method wherein the nanocarrier beads comprise granular substances with an at least partially hydrophilic surface. In a preferred manner, the nanocarrier beads comprise granular silicon oxide, preferably silicon dioxide. As DNA crosslinking is very efficient, particularly good results can be achieved through the use of such beads.

It is also preferred that the granular substances have a grain size of from 10 to 200 nm, preferably 50 nm. The best results were achieved with these grain sizes because the DNA-carrier complex showed surprising stability.

In another preferred embodiment the invention relates to said method wherein the paramagnetic beads comprise a paramagnetic and/or superparamagnetic core and a hydrophilic surface. These properties ensure easy and rapid removal of the complex without requiring the use of particularly strong magnetic fields.

A paramagnetic core is magnetized in an external magnetic field in such a way that the magnetic field is amplified in the interior thereof. Paramagnetism occurs in materials wherein the atoms or molecules have a magnetic moment. In physics all materials with positive magnetic susceptibility and without magnetic order are classified as paramagnetic.

A superparamagnetic core in the meaning of the invention refers to the magnetic properties of very small particles of a ferromagnetic material, which cannot maintain permanent magnetization even at temperatures below the Curie temperature (temperature where ferromagnetic materials lose their permanent magnetic field; the material shows paramagnetic behavior above the Curie temperature). In contrast to a paramagnet, small magnetic particles rather than individual atoms independently change their direction of magnetization.

These properties ensure that a weak magnetic field is sufficient to separate the complex via the magnetizable beads.

In a preferred manner the magnetizable beads, preferably paramagnetic beads, have a size greater than 200 nm, preferably greater than 500 nm, and more preferably 1 to 2 μm. The use of such dimensions ensures that the whole complex and thus the total DNA is removed from the sample. In fact, particles of such a large size are not particularly well suited to crosslink the DNA, because they undergo relatively rapid sedimentation and do not have a particularly large number of binding sites. However, this property is not necessary because the DNA has already been crosslinked via the nanocarrier beads. It is therefore sufficient that the magnetizable beads bind to a few sites on the DNA. Owing to the size of the beads, they have a higher magnetic moment and can easily be removed using conventional magnetic separators.

In a likewise preferred manner the number of nanocarrier beads is higher than the number of paramagnetic beads. The stoichiometric ratio between nanocarrier beads and magnetizable beads is of importance to the success of the method in accordance with the invention. Surprisingly, it was found necessary to use more nanocarrier beads than paramagnetic beads. The precise numerical ratio between the two types of beads is determined by the size ratio of the two types, the magnetic susceptibility of the paramagnetic beads, and the nature of the surfaces. As to the nanocarrier beads, it is preferred to use 0.1% w/v to 15% w/v, more preferably 0.5% w/v to 8% w/v in the lysis/binding buffer, and for the paramagnetic beads 0.01% w/v to 5% w/v, more preferably 0.5% w/v to 1% w/v in the lysis/binding buffer.

Commercially available separators such as the Thermo Electron KingFisher mL instrument are preferably used for magnetic separation.

The principle of magnetic separation is based on separating magnetic from non-magnetic components in a mixture by applying a magnetic field. Separation using magnetizable nano- and microparticles is an easy, rapid and efficient purification technique for separating nucleic acids.

It is also preferred to use magnetizable beads for RNA isolation. Following removal of the DNA from the sample, the RNA can be isolated in a conventional fashion. Paramagnetic beads are particularly suitable to this end. The buffer must be adjusted so as to have good binding conditions for the RNA. It was found that particularly good results can be achieved when the magnetizable beads used in RNA binding are smaller than the magnetizable beads used in DNA binding. It is therefore preferred for RNA binding to use beads with a diameter of 100 nm to 700 nm, more preferably 200 nm to 500 nm. Those skilled in the art will be aware of useful methods without requiring their own inventive activity.

This embodiment is particularly preferred because successful RNA isolation even from very small samples can be effectively ensured.

Any sample containing RNA can be used in accordance with the invention. The biological sample is preferably selected from the group comprising blood samples, tissue samples, cells, stool samples, urine samples, semen, body fluids, plant cells, bacterial lysates, yeasts, whole blood samples and/or food samples.

In addition, any RNA can be isolated. Preferred is a method wherein the isolated RNA is eukaryotic, viral and/or bacterial RNA.

In yet another preferred embodiment, the invention relates to a kit comprising nanocarrier beads and magnetizable beads, preferably paramagnetic beads and/or a mixture of nanocarrier beads and magnetizable beads, preferably paramagnetic beads, for RNA isolation.

In the mixture of both types of particles the number of nanocarrier beads is preferably higher than the number of magnetizable beads, preferably paramagnetic beads. The precise ratio is determined by the size ratio of the two types, the magnetic susceptibility of the paramagnetic beads, and the nature of the surfaces.

Preferably, the kit also comprises lysis buffer, wash buffer, elution buffer and/or ethanol.

The kit of the invention can be used for any type of RNA isolation. Those skilled in the art will know how the buffer solutions must be adapted to the respective samples without requiring inventive activity of their own.

Preferred is a kit comprising two different types of magnetizable beads, i.e. one type for complex formation and one type for RNA binding. In a preferred manner, the magnetizable beads for complex formation, i.e. binding to the DNA, are larger in size than the magnetizable beads for binding the RNA. It was found particularly advantageous when the magnetizable beads for DNA binding have a diameter of 0.8 µm to 2 µm, preferably 1 µm, and the magnetizable beads for RNA binding a diameter of 100 nm to 700 nm, preferably 200 nm to 500 nm.

EXAMPLES

The optimum ratios for the substances used in the examples were determined empirically. For the substances used herein, values of between 0.2% w/v to 10% w/v for the nanocarrier beads in lysis/binding buffer and 0.01% w/v to 2% w/v for the paramagnetic beads in lysis/binding buffer were determined.

Example 1

Isolation of Pure Total RNA from Cells Using Nanocarrier Beads from Invitek

An RNA lysis buffer including 5 M guanidine isothiocyanate, 10 mM 1,4-dithiothreitol, 10 mM sodium citrate and 10% N-lauroylsarcosine is added with 10 g/l nanocarrier beads 50 nm in diameter. 500,000 3T3 fibroblast cells from cell culture are dissolved in this buffer. In a magnetic separator (KingFisher mL Thermo Electron) the DNA is removed by binding using paramagnetic beads (diameter: 1 µm; Invitek MAP A solution). Following addition of a binding buffer, the RNA is removed from the residue by binding via paramagnetic beads (diameter: 250 nm; Invitek SNAP solution), washed and eluted.

Loading the magnetic separator:
$1^{st}$ row: $5·10^5$ 3T3 cells in 700 µl of TR lysis solution (1, 3 and 4 without nanocarrier beads)+7 µl of DTT (+20 µl of MAP solution A)
$2^{nd}$ row: 800 µl of $H_2O$
$3^{rd}$ row: 800 µl of wash buffer RI
$4^{th}$ row: 800 µl of wash buffer RII
$5^{th}$ row: 100 µl of elution buffer R
after $1^{st}$ binding and removal of MAP solution A in row 2
row 1: 500 µl of ethanol+20 µl of SNAP solution FIG. 1 shows the gel with the following load:
M: Length standard
1: Lysis buffer
2: Lysis buffer with nanocarrier beads
3: Lysis buffer with MAP solution A
4: Lysis buffer with MAP solution A
5: Lysis buffer with nanocarrier beads and MAP solution A
6: Lysis buffer with nanocarrier beads and MAP solution A
7: Lysis buffer with nanocarrier beads and MAP solution A
8: Lysis buffer with nanocarrier beads and MAP solution A Complete removal of the DNA can be seen on the gel when using a combination of paramagnetic beads and nanocarrier beads, while paramagnetic beads alone or nanocarrier beads alone cannot achieve this.

Example 2

Isolation of Pure Total RNA from Cells Using Beads from Other Manufacturers

An RNA lysis buffer including 5 M guanidine isothiocyanate, 10 mM 1,4-dithiothreitol, 10 mM sodium citrate and 10% N-lauroylsarcosine is added with 20 g/l nanocarrier beads 50 nm in diameter. 500,000 3T3 fibroblast cells from cell culture are dissolved in this buffer. In a magnetic separator (KingFisher mL Thermo Electron) the DNA is removed by binding using paramagnetic beads (diameter: 1.5 µm; Invitek MAP A solution). Following addition of a binding buffer, the RNA is removed from the residue by binding via paramagnetic beads (diameter: 250 nm; Invitek SNAP solution), washed and eluted.

Loading the magnetic separator:
$1^{st}$ row: $5·10^5$ 3T3 cells in 700 µl of TR lysis solution (1 and 4 without nanocarrier beads)+7 µl of DTT (+20 µl of commercial beads from a: Chemicell, b: Micromod)
$2^{nd}$ row: 800 µl of $H_2O$
$3^{rd}$ row: 800 µl of wash buffer RI
$4^{th}$ row: 800 µl of wash buffer RII
$5^{th}$ row: 100 µl of elution buffer R
after $1^{st}$ binding and removal of bead solution in row 2
row 1: 500 µl of ethanol+20 µl of SNAP solution
paramagnetic beads A: Chemicell: SIMAG/MP-DNA, diameter 2 µm, 200 mg/ml FIG. 2 shows the gel with the following load:
M: Length Standard
1: Lysis buffer with Chemicell beads
2: Lysis buffer with nanocarrier beads and beads A
3: Lysis buffer with nanocarrier beads and beads A Complete removal of DNA can be seen on the gel when using beads A. The paramagnetic beads alone barely remove any DNA.

Example 3

Isolation of Pure Total RNA from Liver Tissue Using Beads from Invitek

An RNA lysis buffer including 5 M guanidine isothiocyanate, 10 mM 1,4-dithiothreitol, 10 mM sodium citrate and 10% N-lauroylsarcosine is added with 10 g/l nanocarrier beads 50 nm in diameter. 10 mg or 20 mg of rat liver is homogenized in this buffer via zirconia beads. In a magnetic separator (KingFisher mL Thermo Electron) the DNA is removed by binding using paramagnetic beads (diameter: 1 µm; Invitek MAP A solution). Following addition of a binding buffer, the RNA is removed from the residue by binding via paramagnetic beads (diameter: 250 nm; Invitek SNAP solution), washed and eluted.

Loading the magnetic separator:
$1^{st}$ row: 10 mg or 20 mg of rat liver in 700 µl of TR lysis solution (1 and 5 without nanocarrier beads)+7 µl of DTT (+20 µl of MAP solution A)
$2^{nd}$ row: 800 µl of $H_2O$
$3^{rd}$ row: 800 µl of wash buffer RI
$4^{th}$ row: 800 µl of wash buffer RII
$5^{th}$ row: 100 µl of elution buffer R
after $1^{st}$ binding and removal of MAP solution A in row 2
row 1: 500 µl of ethanol+20 µl of SNAP solution FIG. 3 shows the gel with the following load:
M: Length standard
1: 10 mg of liver lysis buffer with MAP solution A
2: 10 mg of liver lysis buffer with nanocarrier beads and MAP solution A
3: 10 mg of liver lysis buffer with nanocarrier beads and MAP solution A
4: 10 mg of liver lysis buffer with nanocarrier beads and MAP solution A
5: 20 mg of liver lysis buffer with MAP solution A
6: 20 mg of liver lysis buffer with nanocarrier beads and MAP solution A
7: 20 mg of liver lysis buffer with nanocarrier beads and MAP solution A
8: 20 mg of liver lysis buffer with nanocarrier beads and MAP solution A Complete removal of DNA can be seen on the gel. The paramagnetic beads alone barely remove any DNA.

Example 4

The functionality of the new RNA protocol in furnishing DNA-free RNA using various tissues as starting materials is examined in the following tests. The aim was to determine the employed maximum amount of starting tissue as a function of various tissue materials. The background is that a defined amount of materials for the complex (20 µl of MAP A paramagnetic particles 5-10 µm in diameter, 400 mg/ml, and 20 µl of carrier, 100 mg/ml silicate particles for complex formation, diameter less than 50 nm) can only bind a defined amount of DNA that is defined by the supplied sample material.

All tests proceed as follows:
The tissue is lysed in 0.7 ml of TR lysis buffer (per se known lysis buffer for RNA samples on chaotropic salt basis). This is done in a tissue grinder after addition of 7 µl of DTT, 20 µl of MAP A (paramagnetic particles 5-10 µm in diameter, 400 mg/ml) and 20 µl of carrier (100 mg/ml silicate particles for complex formation, less than 50 nm in diameter).

From this point on, the protocol proceeds automatically in an automated KingFisher ml (Thermo electronics) laboratory robot. See machine protocol (machine protocol KingFisher ml.doc).

The machine is loaded as follows:
$1^{st}$ tube free
$2^{nd}$ tube 800 µl of RNase-free water
$3^{rd}$ tube 800 µl of high-salt wash buffer: 50% ethanol, 1.5 M guanidine isothiocyanate
$4^{th}$ tube 800 µl of low-salt wash buffer: 80% ethanol, pH 8 Tris-HCl buffered
$5^{th}$ tube 100 µl of RNase-free water After the first step on the machine, i.e. removal of the DNA complex, well 1 is added with another 20 µl of SNAP solution (paramagnetic particles 200-500 nm in diameter, 25 mg/ml).

The result of the tests is that different maximum amounts for different starting materials can be used for successful preparation of DNA-free RNA: liver up to 30 mg, intestine up to 10 mg, stomach up to 25 mg, brain up to 40 mg, kidney up to 30 mg. When exceeding these maximum amounts, the fluid volumes of the protocol must be extrapolated proportionally.

| Tissue | Amount[mg] | MAP-A [µl] | Carrier [µl] |
|---|---|---|---|
| Liver | up to 30 | 20 | 20 |
| Intestine | up to 10 | 20 | 20 |
| Brain | up to 40 | 20 | 20 |
| Kidney | up to 30 | 20 | 20 |
| Stomach | up to 25 | 20 | 20 |

Machine Protocol:
1) Binding the DNA via a complex in well 1
   Well 1 contains 0.7 ml of lysis buffer, 20 µl of carrier, 20 µl of MAP solution A, 7 µl of DTT, and sample.
2) Transferring the DNA complex into well 2 to remain therein
3) Manual addition of 20 µl of SNAP solution and 500 µl of ethanol to well 1
4) Binding the RNA in well 1
   At this point in time well 1 contains 0.7 ml of lysis buffer, 7 µl of DTT, the residual material of the sample, 500 µl of ethanol and 20 µl of SNAP solution
5) Washing of the RNA in well 3
   At this point in time, well 3 contains 0.8 ml of wash buffer (wash buffer R1)
6) Washing of the RNA in well 4
   At this point in time, well 4 contains 0.8 ml of wash buffer (wash buffer R2)
7) Drying of the beads with bound RNA (outside the wells)
8) Eluting the RNA in well 5
   At this point in time, well 5 contains 0.15 ml of elution buffer (elution buffer R).

1. Test Using Rat Liver
Material:
Substance/Solution
20 µl of MAP-A solution, paramagnetic particles for DNA binding
20 µl of SNAP solution, paramagnetic particles for RNA binding
700 µl of TR lysis solution with no carrier
7 µl of 1 M DTT
500 µl of ethanol
800 µl of wash buffer R1
800 ml of wash buffer R2

Figure 7:
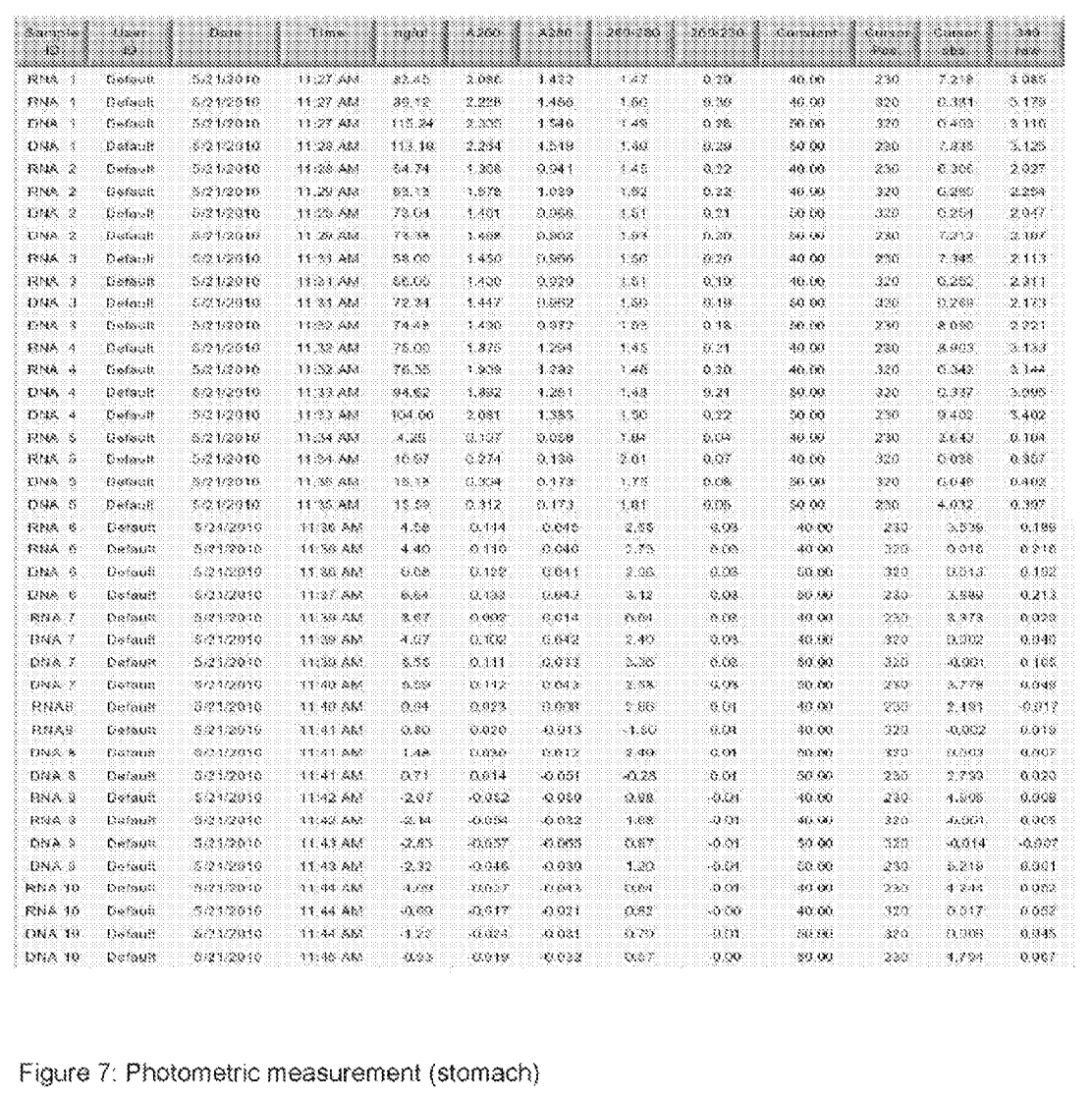

100 ml of MilliQ
1 µl of formamide
2 µl of Orange G
Implementation:
Preparations for Precise Measurement of Amounts:
   Weigh empty tubes
   Freeze tubes, then load with tissue (varying amounts)
   Place tubes in liquid nitrogen and re-weigh
   Re-freeze tubes
Loading the KingFisher Plastic
   1. Tube 1 free
   2. Tube 2 800 µl of MilliQ
   3. Tube 3 800 µl of wash buffer R1
   4. Tube 4 800 µl of wash buffer R2
   5. Tube 5 100 µl of MilliQ
Lysing the Cells
   Fetch tissue in frozen vessels
   Add 700 µl of TR lysis solution with no carrier, 7 µl of DTT, 20 µl of MAP A and 20 µl of carrier (buffer freezes immediately)
   Thaw samples in water
   Lyse for 2 min at level 8 in Bullet Blender (tissue grinder)
Purification
   Place sample in tube 1
   Launch InviMAG_10 program
   During Pause On, fill 500 µl of ethanol and 20 µl of SNAP in tube 1
   When complete, quickly remove eluate from tube 5 and fill in new Eppendorf tube
Measurement and Gel Analysis
   Mix 15 µl of sample with 1 µl of formamide and denature for 10 min at 70° C.
   Add 2 µl of Orange G and place sample on RNA gel
   Run for 12 min at 100 V
Evaluation:
   FIG. 4 shows the gel loaded as follows:
01=30 mg
02=11 mg
03=14 mg
04=13 mg
05=22 mg
06=10 mg
07=14 mg
08=17 mg
09=22 mg
10=18 mg
   The corresponding photometric measurement is shown in FIG. 5.
2. Test Using Rat Stomach Tissue
Material
Substance/Solution
20 µl of MAP-A solution, paramagnetic particles for DNA binding
20 µl of SNAP solution, paramagnetic particles for RNA binding
700 µl of TR lysis solution with no carrier
7 µl of 1 M DTT
500 µl of ethanol
800 µl of wash buffer R1
800 ml of wash buffer R2
100 ml of MilliQ
1 µl of formamide
2 µl of Orange G
Implementation:
Preparations for Precise Measurement of Amounts:
   Weigh empty tubes
   Freeze tubes, then load with tissue (varying amounts)
   Place tubes in liquid nitrogen and re-weigh
   Re-freeze tubes
Loading the KingFisher Plastic
   1. Tube 1 free
   2. Tube 2 800 µl of MilliQ
   3. Tube 3 800 µl of wash buffer R1
   4. Tube 4 800 µl of wash buffer R2
   5. Tube 5 100 µl of MilliQ
Lysing the Cells
   Fetch tissue in frozen vessels
   Add 700 µl of TR lysis solution with no carrier, 7 µl of DTT, 20 µl of MAP A and 20 µl of carrier (buffer freezes immediately)
   Thaw samples in water
   Lyse for 2 min at level 8 in Bullet Blender (tissue grinder)
Purification
   Place sample in tube 1
   Launch InviMAG_10 program
   During Pause On, fill 500 µl of ethanol and 20 µl of SNAP in tube 1
   When complete, quickly remove eluate from tube 5 and fill in new Eppendorf tube
Measurement and Gel Analysis
   Mix 15 µl of sample with 1 µl of formamide and denature for 10 min at 70° C.
   Add 2 µl of Orange G and place sample on RNA gel
   Run for 12 min at 100 V
Evaluation:
   FIG. 6 shows the gel loaded as follows:
01=24 mg
02=26 mg
03=25 mg
04=43 mg excessive amount
05=44 mg excessive amount
06=39 mg
07=42 mg excessive amount
08=25 mg
09=19 mg
10=20 mg
   The corresponding photometric measurement is shown in FIG. 7.
3. Test Using Rat Kidney Tissue
Material
Substance/Solution
20 µl of MAP-A solution, paramagnetic particles for DNA binding
20 µl of SNAP solution, paramagnetic particles for RNA binding
700 µl of TR lysis solution with no carrier
7 µl of 1 M DTT
500 µl of ethanol
800 µl of wash buffer R1
800 ml of wash buffer R2
100 ml of MilliQ
1 µl of formamide
2 µl of Orange G
Implementation:
Preparations for Precise Measurement of Amounts:
   Weigh empty tubes
   Freeze tubes, then load with tissue (varying amounts)
   Place tubes in liquid nitrogen and re-weigh
   Re-freeze tubes
Loading the KingFisher Plastic
   1. Tube 1 free
   2. Tube 2 800 µl of MilliQ
   3. Tube 3 800 µl of wash buffer R1
   4. Tube 4 800 µl of wash buffer R2

Figure 9:
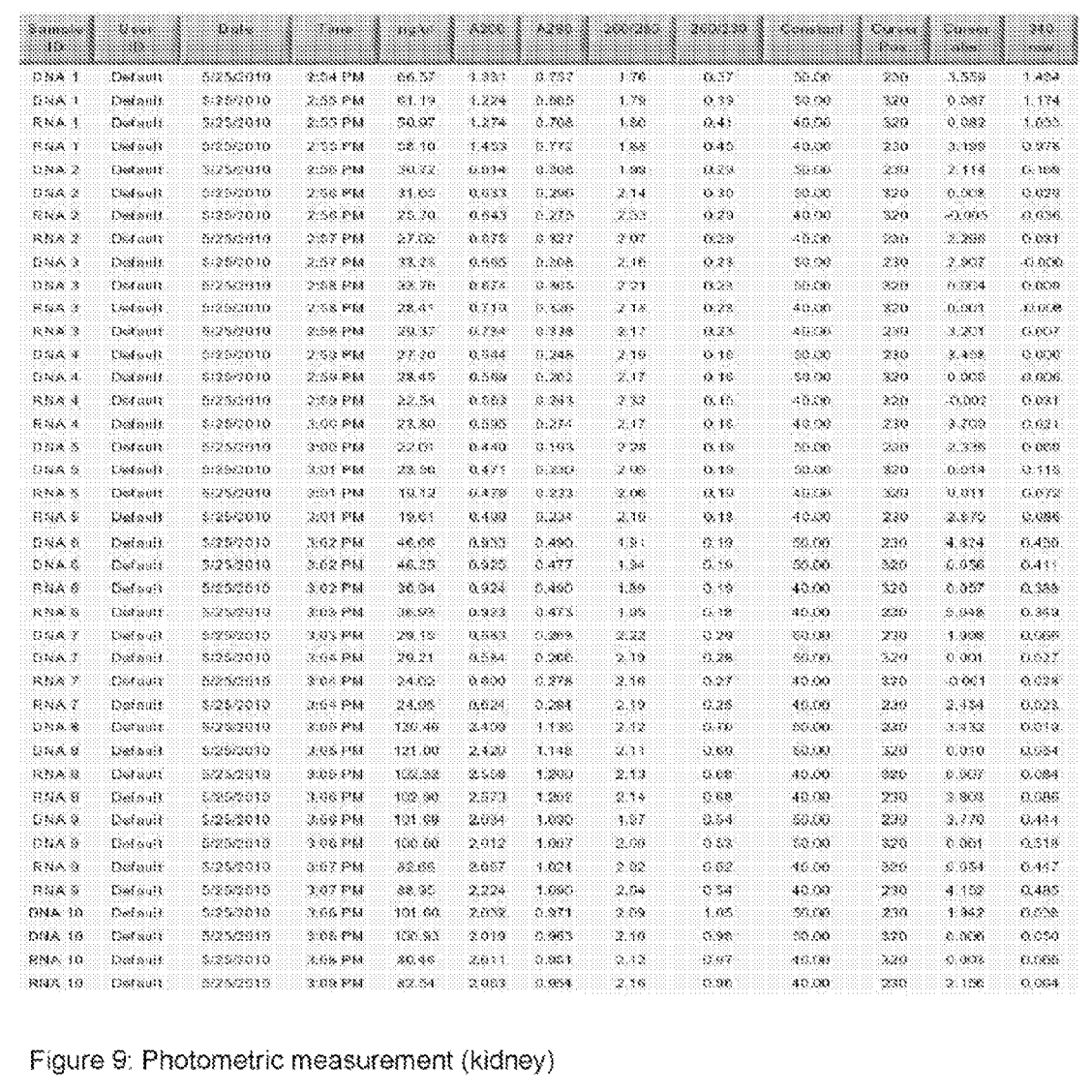
Figure 11:
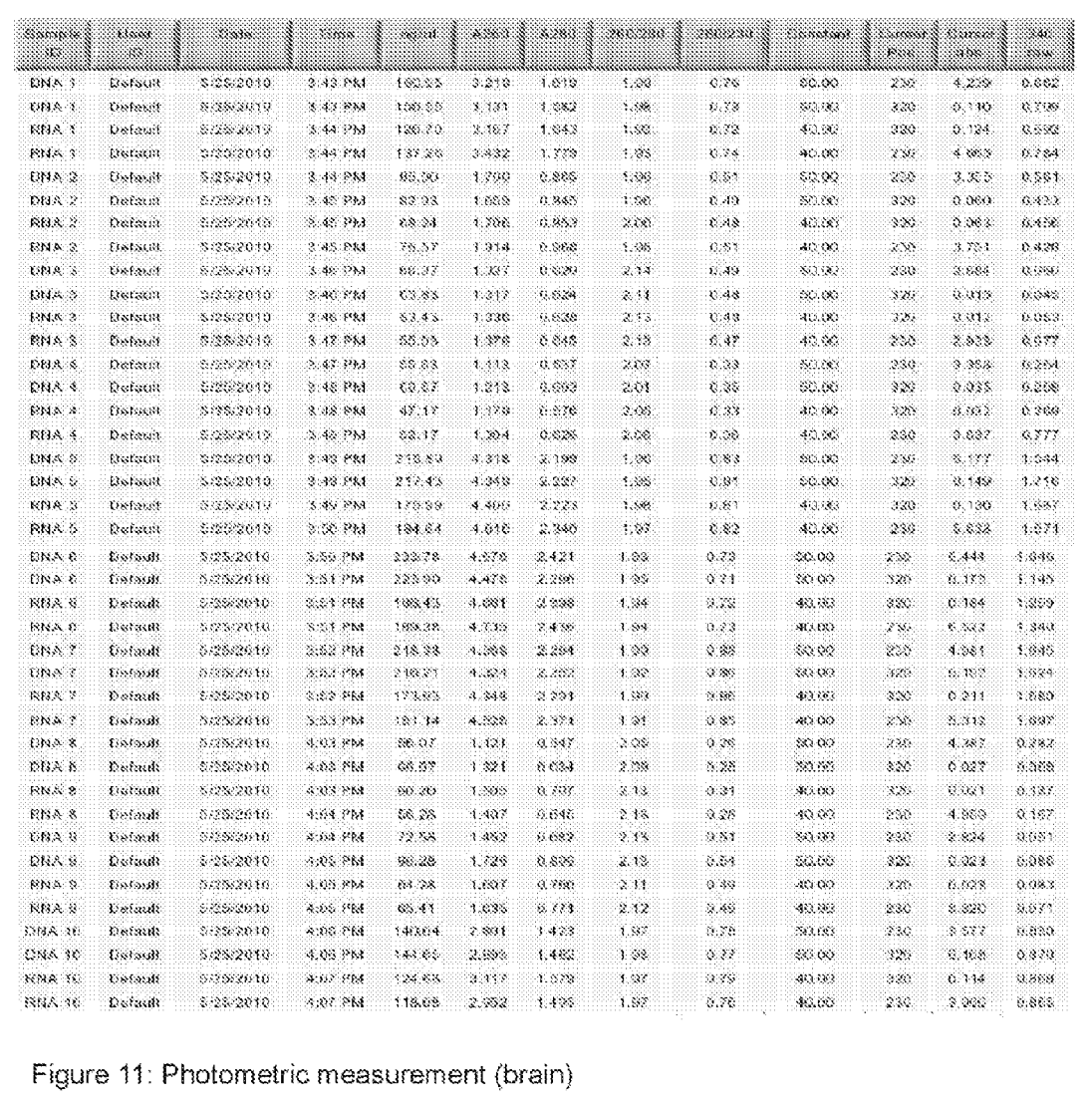

5. Tube 5 100 µl of MilliQ
Lysing the Cells
　Fetch Tissue in Frozen Vessels
　Add 700 µl of TR lysis solution with no carrier, 7 µl of DTT, 20 µl of MAP A and 20 µl of carrier (buffer freezes immediately)
　Thaw samples in water
　Lyse for 2 min at level 8 in Bullet Blender (tissue grinder)
Purification
　Place sample in tube 1
　Launch InviMAG_10 program
　During Pause On, fill 500 µl of ethanol and 20 µl of SNAP in tube 1
　When complete, quickly remove eluate from tube 5 and fill in new Eppendorf tube
Measurement and Gel Analysis
　Mix 15 µl of sample with 1 µl of formamide and denature for 10 min at 70° C.
　Add 2 µl of Orange G and place sample on RNA gel
　Run for 12 min at 100 V
Evaluation:
　FIG. 8 shows the gel loaded as follows:
01=16 mg
02=19 mg
03=18 mg
04=33 mg
05=18 mg
06=26 mg
07=22 mg
08=25 mg
09=20 mg
10=37 mg excessive amount
　The result of the corresponding photometric measurement is shown in FIG. 9.
4. Test Using Rat Brain Tissue
Material
Substance/Solution
20 µl of MAP-A solution, paramagnetic particles for DNA binding
20 µl of SNAP solution, paramagnetic particles for RNA binding
700 µl of TR lysis solution with no carrier
7 µl of 1 M DTT
500 µl of ethanol
800 µl of wash buffer R1
800 ml of wash buffer R2
100 ml of MilliQ
1 µl of formamide
2 µl of Orange G
Implementation:
Preparations for Precise Measurement of Amounts:
　Weigh empty tubes
　Freeze tubes, then load with tissue (varying amounts)
　Place tubes in liquid nitrogen and re-weigh
　Re-freeze tubes
Loading the KingFisher Plastic
　1. Tube 1 free
　2. Tube 2 800 µl of MilliQ
　3. Tube 3 800 µl of wash buffer R1
　4. Tube 4 800 µl of wash buffer R2
　5. Tube 5 100 µl of MilliQ
Lysing the Cells
　Fetch tissue in frozen vessels
　Add 700 µl of TR lysis solution with no carrier, 7 µl of DTT, 20 µl of MAP A and 20 µl of carrier (buffer freezes immediately)
　Thaw samples in water
　Lyse for 2 min at level 8 in Bullet Blender (tissue grinder)
Purification
　Place sample in tube 1
　Launch InviMAG_10 program
　During Pause On, fill 500 µl of ethanol and 20 µl of SNAP in tube 1
　When complete, quickly remove eluate from tube 5 and fill in new Eppendorf tube
Measurement and Gel Analysis
　Mix 15 µl of sample with 1 µl of formamide and denature for 10 min at 70° C.
　Add 2 µl of Orange G and place sample on RNA gel
　Run for 12 min at 100 V
Evaluation:
　FIG. 10 shows the gel loaded as follows:
01=43 mg excessive amount
02=24 mg
03=33 mg
04=26 mg
05=31 mg
06=37 mg
07=33 mg
08=24 mg
09=27 mg
10=28 mg
　The result of the corresponding photometric measurement is shown in FIG. 11.
5. Test Using Rat Intestinal Tissue
Material
Substance/Solution
20 µl of MAP-A solution, paramagnetic particles for DNA binding
20 µl of SNAP solution, paramagnetic particles for RNA binding
700 µl of TR lysis solution with no carrier
7 µl of 1 M DTT
500 µl of ethanol
800 µl of wash buffer R1
800 ml of wash buffer R2
100 ml of MilliQ
1 µl of formamide
2 µl of Orange G
Implementation:
Preparations for Precise Measurement of Amounts:
　Weigh empty tubes
　Freeze tubes, then load with tissue (varying amounts)
　Place tubes in liquid nitrogen and re-weigh
　Re-freeze tubes
Loading the KingFisher Plastic
　1. Tube 1 free
　2. Tube 2 800 µl of MilliQ
　3. Tube 3 800 µl of wash buffer R1
　4. Tube 4 800 µl of wash buffer R2
　5. Tube 5 100 µl of MilliQ
Lysing the Cells
　Fetch tissue in frozen vessels
　Add 700 µl of TR lysis solution with no carrier, 7 µl of DTT, 20 µl of MAP A and 20 µl of carrier (buffer freezes immediately)
　Thaw samples in water
　Lyse for 2 min at level 8 in Bullet Blender (tissue grinder)
Purification
　Place sample in tube 1
　Launch InviMAG_10 program
　During Pause On, fill 500 µl of ethanol and 20 µl of SNAP in tube 1

When complete, quickly remove eluate from tube 5 and fill in new Eppendorf tube

Measurement and Gel Analysis

Mix 15 μl of sample with 1 μl of formamide and denature for 10 min at 70° C.

Add 2 μl of Orange G and place sample on RNA gel

Run for 12 min at 100 V

Evaluation:

FIG. 12 shows the gel loaded as follows:

1=13 mg
2=09 mg
3=35 mg excessive amount
4=04 mg
5=20 mg

The result of the corresponding photometric measurement is shown in FIG. 13.

The invention claimed is:

1. A method for purifying RNA from a biological sample comprising at least double stranded DNA and single-stranded RNA, said method comprising contacting the sample comprising said DNA and said RNA with a lysis buffer, nanocarrier beads and magnetizable beads under conditions suitable for formation of a complex comprising said nanocarrier beads, said DNA and said magnetizable beads, thereby forming a first mixture comprising said complex, wherein said lysis buffer:

is configured to provide said conditions suitable for formation, upon said contacting the sample comprising said DNA and said RNA with said lysis buffer, said nanocarrier beads and said magnetizable beads, of said complex comprising said nanocarrier beads, said DNA and said magnetizable beads, wherein, under said conditions, said DNA binds said nanocarrier beads and said magnetizable beads and wherein said complex does not comprise the RNA; and comprises an aqueous salt solution with a salt concentration of greater than 1M, applying a magnetic field to said first mixture, separating and removing said complex comprising said nanocarrier beads, said DNA and said magnetizable beads from the said first mixture via the magnetic field and forming a second mixture, subsequently adding a binding buffer to said second mixture, and purifying said RNA from said second mixture and obtaining purified RNA.

2. The method as claimed in claim 1, wherein said purified RNA is obtained by binding said RNA to magnetizable beads from the binding buffer.

3. The method of claim 2, wherein the magnetizable beads are paramagnetic beads for RNA binding that have a diameter of 100 nm to 700 nm.

4. The method as claimed in claim 1,
wherein the purified RNA is essentially free of DNA.

5. The method according to claim 1,
wherein the nanocarrier beads comprise granular substances with an at least partially hydrophilic surface.

6. The method according to claim 5,
wherein the granular substances have a grain size of from 10 to 200 nm.

7. The method of claim 6, wherein the granular substances have a grain size of 50 nm.

8. The method according to claim 1, wherein the nanocarrier beads are substantially non-magnetic.

9. The method of claim 8, wherein the silicon oxide is silicon dioxide.

10. The method according to claim 1,
wherein the magnetizable beads are paramagnetic beads which comprise a paramagnetic and/or superparamagnetic core and a hydrophilic surface.

11. The method according to claim 1,
wherein the magnetizable beads are greater than 200 nm in size.

12. The method of claim 11 wherein the magnetizable beads are paramagnetic beads for DNA binding that have a diameter of 0.8 μm to 2 μm.

13. The method according to claim 1,
wherein the magnetizable beads comprise an iron oxide core and/or a surface of silicon oxide.

14. The method according to claim 1,
wherein the number of said nanocarrier beads is higher than the number of said magnetizable beads.

15. The method according to claim 1,
wherein the biological sample is selected from the group consisting of blood samples, tissue samples, cells, stool samples, urine samples, semen, body fluids, plant cells, bacterial lysates, yeasts, whole blood samples and/or food samples.

16. The method according to claim 1,
wherein the purified RNA is eukaryotic, viral and/or bacterial RNA.

17. The method of claim 1, wherein said magnetizable beads are paramagnetic beads.

* * * * *